United States Patent
Sekiguchi et al.

(10) Patent No.: US 12,291,461 B2
(45) Date of Patent: *May 6, 2025

(54) CERIUM OXIDE NANOPARTICLE, DISPERSION BODY, OXIDANT, ANTIOXIDANT, AND METHOD OF PRODUCING CERIUM OXIDE NANOPARTICLE

(71) Applicant: Toray Industries, Inc., Tokyo (JP)

(72) Inventors: Shota Sekiguchi, Kamakura (JP); Takahiro Motoshiromizu, Kamakura (JP); Masateru Ito, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 392 days.

This patent is subject to a terminal disclaimer.

(21) Appl. No.: 17/788,687

(22) PCT Filed: Dec. 25, 2020

(86) PCT No.: PCT/JP2020/048918
§ 371 (c)(1),
(2) Date: Jun. 23, 2022

(87) PCT Pub. No.: WO2021/132928
PCT Pub. Date: Jul. 1, 2021

(65) Prior Publication Data
US 2023/0030648 A1    Feb. 2, 2023

(30) Foreign Application Priority Data

Dec. 26, 2019   (JP) ................... 2019-236819

(51) Int. Cl.
| | | |
|---|---|---|
| C01F 17/206 | (2020.01) | |
| C01F 17/235 | (2020.01) | |
| C02F 1/72 | (2023.01) | |
| C09K 15/02 | (2006.01) | |
| C09K 15/30 | (2006.01) | |
| C02F 101/30 | (2006.01) | |

(52) U.S. Cl.
CPC .............. *C01F 17/235* (2020.01); *C02F 1/72* (2013.01); *C09K 15/02* (2013.01); *C09K 15/30* (2013.01); *C01P 2004/64* (2013.01); *C02F 2101/308* (2013.01)

(58) Field of Classification Search
CPC ...... C01F 17/235; C01F 17/00; C01F 17/206; C02F 1/72; C02F 2101/308; C09K 15/02; C09K 15/30; C01P 2004/64; A61K 33/244
See application file for complete search history.

(56) References Cited

U.S. PATENT DOCUMENTS

| | | | |
|---|---|---|---|
| 7,504,356 | B1 | 3/2009 | Self et al. |
| 2007/0092423 | A1 | 4/2007 | Hyeon et al. |
| 2010/0152077 | A1 | 6/2010 | Allston et al. |
| 2013/0195927 | A1* | 8/2013 | Sudipta ............... A61K 33/244 |
| | | | 424/617 |
| 2013/0196167 | A1* | 8/2013 | Kataoka ................. C09D 7/67 |
| | | | 106/287.18 |
| 2014/0271899 | A1 | 9/2014 | Leiter et al. |
| 2015/0079162 | A1 | 3/2015 | Hyeon et al. |
| 2017/0105941 | A1 | 4/2017 | Imam |
| 2018/0325832 | A1 | 11/2018 | Bell |

FOREIGN PATENT DOCUMENTS

| | | |
|---|---|---|
| CN | 100998335 A | 7/2007 |
| CN | 102281945 A | 12/2011 |
| CN | 102285678 A | 12/2011 |
| JP | 2009-511403 A | 3/2009 |
| JP | 2015-518480 A | 7/2015 |
| JP | 2016-514163 A | 5/2016 |
| JP | 2017-525658 A | 9/2017 |
| JP | 2018-508568 A | 3/2018 |

OTHER PUBLICATIONS

Improving the anticorrosive performance of epoxy coatings by embedding various percentages of unmodified and imidazole modified CeO2 nanoparticles, Hosseini et al (Progress in Organic Coatings 122 (2018) 56-63) .*

First Office Action dated Jun. 22, 2023, of counterpart Chinese Patent Application No. 202080089685.5, along with an English machine translation.

International Search Report dated Feb. 2, 2021, of corresponding International Application No. PCT/JP2020/048918, along with an English translation.

Asati, A. et al., "Oxidase-Like Activity of Polymer-Coated Cerium Oxide Nanoparticles," *Angewandte Chemie Int. Ed.*, 2009, vol. 48, pp. 2308-2312.

Xue, Y. et al., "Direct Evidence for Hydroxyl Radical Scavenging Activity of Cerium Oxide Nanoparticles," *The Journal of Physical Chemistry C*, 2011, vol. 115, pp. 4433-4438.

* cited by examiner

Primary Examiner — Haidung D Nguyen
(74) Attorney, Agent, or Firm — DLA Piper LLP (US)

(57) ABSTRACT

A cerium oxide nanoparticle is produced by mixing a solution of an aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in a ring structure of the aromatic heterocyclic compound, with a solution containing a cerium (III) ion or with a cerium (III) salt, followed by addition of an oxidant.

14 Claims, 2 Drawing Sheets

CERIUM OXIDE NANOPARTICLE, DISPERSION BODY, OXIDANT, ANTIOXIDANT, AND METHOD OF PRODUCING CERIUM OXIDE NANOPARTICLE

TECHNICAL FIELD

This disclosure relates to a cerium oxide nanoparticle, a dispersion body containing the nanoparticle, a method of producing the cerium oxide nanoparticle, and an oxidant and an antioxidant containing the cerium oxide nanoparticle or the dispersion body.

BACKGROUND

Under the circumstances of increase in concerns with safety and hygiene management in recent years, an antibacterial technology to decompose a harmful substance and a microorganism is receiving attention. For example, titanium dioxide has the property of oxidatively decomposing an organic substance through its photocatalytic characteristics, which is evaluated in the decomposition reaction of an organic dye. Such oxidative decomposition characteristics are expected to be used, besides the use as an antibacterial agent, also for decomposition of low-molecular weight substances such as acetaldehyde and ammonia, as well as various harmful substances such as an allergen and a virus.

On the other hand, a cerium oxide nanoparticle (nanoceria) has catalytic activities similar to those of oxidative and reductive enzymes such as a catalase, an oxidase, a peroxidase, and a superoxide dismutase. Thus, it is expected to be used as an oxidant and an antioxidant. Because such catalytic activities do not require a special light source such as an ultraviolet light, the cerium oxide nanoparticle is expected to be used for the uses different from those of titanium dioxide.

However, because the nanoparticles are generally prone to aggregate, during the synthesis thereof, a method is used to stably disperse the obtained nanoparticles by coexisting a compound that serves as a stabilizing agent. In the cerium oxide nanoparticle, for example, a particle dispersion solution is obtained by oxidizing a cerium (III) ion with hydrogen peroxide using polyacrylic acid as a stabilizing agent, or by alkaline neutralization of a cerium (III) ion in an aqueous ammonia using dextran as a stabilizing agent.

In A. Asati, Angew. Chem. Int. Ed. 2009, 48, 2308-2312, a method of synthesizing the cerium oxide nanoparticle whose surface is covered with polyacrylic acid or with dextran is described. A. Asati, Angew. Chem. Int. Ed. 2009, 48, 2308-2312 discloses, among other things, that when polyacrylic acid is used as the stabilizing agent, an oxidase activity, which is a value indicative of the oxidative performance, increases.

In addition, Japanese Translation of PCT International Application No. 2015-518480 describes a synthesis method using pyridine as a reaction solvent upon preparation of a ceria nanoparticle encapsulated with a surfactant such as oleylamine. It discloses that the ceria nanoparticle that is synthesized in such a way is further capped with polyethyleneglycol phospholipid to form a complex, thereby becoming water soluble and having a catalase activity, which is the characteristic indicative of an antioxidative performance.

Furthermore, Japanese Translation of PCT International Application No. 2017-525658 describes a method of synthesizing a composite of nicotine adsorbed to the nanoceria; nicotine being a compound that has pyridine in its substructure. It discloses that the complex can be used to treat neurodegenerative disorder as a biological antioxidant.

In addition, Japanese Translation of PCT International Application No. 2018-508568 describes a method of synthesizing the cerium oxide nanoparticle whose surface is covered with a chelating agent such as citric acid and ethylenediaminodisuccinic acid (EDDS). In particular, it discloses that when citric acid/EDDS is used as the stabilizing agent, the catalase activity, which is a value indicative of the antioxidative performance, increases.

We investigated application of the oxidative and antioxidative performances of the cerium oxide nanoparticle. However, when the oxidative performance was examined in the way as the later-described Comparative Examples, the oxidative degradation of an organic dye using the cerium oxide nanoparticle whose surface is covered with polyacrylic acid as described in A. Asati, Angew. Chem. Int. Ed. 2009, 48, 2308-2312 and commercially available cerium oxide nanoparticles resulted in a low degradation rate. As for the antioxidative performance, as can be seen in the Comparative Examples described later, there is a problem of a low catalase activity in the ceria nanoparticle composite produced by the method described in Japanese Translation of PCT International Application No. 2015-518480. As can be seen in the Comparative Examples described later, the low catalase activity was also observed in the dispersion solution obtained by the production method with reference to Japanese Translation of PCT International Application No. 2017-525658 in which pyridine was post-added and adsorbed onto the cerium oxide nanoparticle, and by the production method described in Japanese Translation of PCT International Application No. 2018-508568 in which a stabilizing agent that is different from that of our dispersion solution was used. On the basis of such results, we sought to find cerium oxide nanoparticles having high oxidative and antioxidative performances.

SUMMARY

We focused on a method of producing the cerium oxide nanoparticle, especially on the stabilizing agent. We found that when the oxidative degradation of an organic dye was attempted using a dispersion body containing a cerium oxide nanoparticle produced by mixing a solution of an aromatic heterocyclic compound with a solution containing a cerium (III) ion or with a cerium (III) salt followed by addition of an oxidant, a higher degradation rate was obtained. The dispersion body produced in this way was found to have high catalase activity and radical scavenging capacity, which are indicative of the antioxidative performance.

We Thus Provide:
(1) A cerium oxide nanoparticle produced by mixing a solution of an aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in a ring structure of the aromatic heterocyclic compound, with a solution containing a cerium (III) ion or with a cerium (III) salt, followed by addition of an oxidant.
(2) The cerium oxide nanoparticle according to (1), wherein a pH is adjusted to 5 or higher at the time when the oxidant is added.

(3) The cerium oxide nanoparticle according to (1) or (2), wherein the aromatic heterocyclic compound is a monocyclic or a bicyclic compound having a five-membered and/or a six-membered ring structure.

(4) The cerium oxide nanoparticle according to any one of (1) to (3), wherein the compound is pyrazole, imidazole, triazole, pyridine, pyridazine, pyrimidine, pyrazine, triazine, tetrazine, indazole, benzimidazole, azaindole, pyrazolopyrimidine, purine, benzotriazole, quinoxaline, cinnoline, quinazoline, phthalazine, naphthyridine, or pteridine.

(5) A cerium oxide nanoparticle comprising: an aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in a ring structure of the aromatic heterocyclic compound, wherein the cerium oxide nanoparticle has maximum absorptions of 5726.0 eV to 5729.0 eV and 5735.0 eV to 5739.0 eV in a CeL3 edge XANES spectrum obtained by an X-ray absorption fine structure spectroscopy.

(6) A dispersion body comprising the cerium oxide nanoparticle according to any one of (1) to (5).

(7) An oxidant comprising the cerium oxide nanoparticle according to any one of (1) to (5) or the dispersion body according to (6).

(8) An antioxidant comprising the cerium oxide nanoparticle according to any one of (1) to (5) or the dispersion body according to (6).

(9) A method of producing a cerium oxide nanoparticle, the method comprising: mixing a solution of an aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in a ring structure of the aromatic heterocyclic compound, with a solution containing a cerium (III) ion or with a cerium (III) salt; and adding an oxidant.

The dispersion body containing the cerium oxide nanoparticle enables oxidative decomposition of a harmful substance with a higher yield than that of conventional cerium oxide nanoparticles, and also enables scavenging a reactive species with a higher yield than that of conventional cerium oxide nanoparticles.

DETAILED DESCRIPTION

Figure 1:
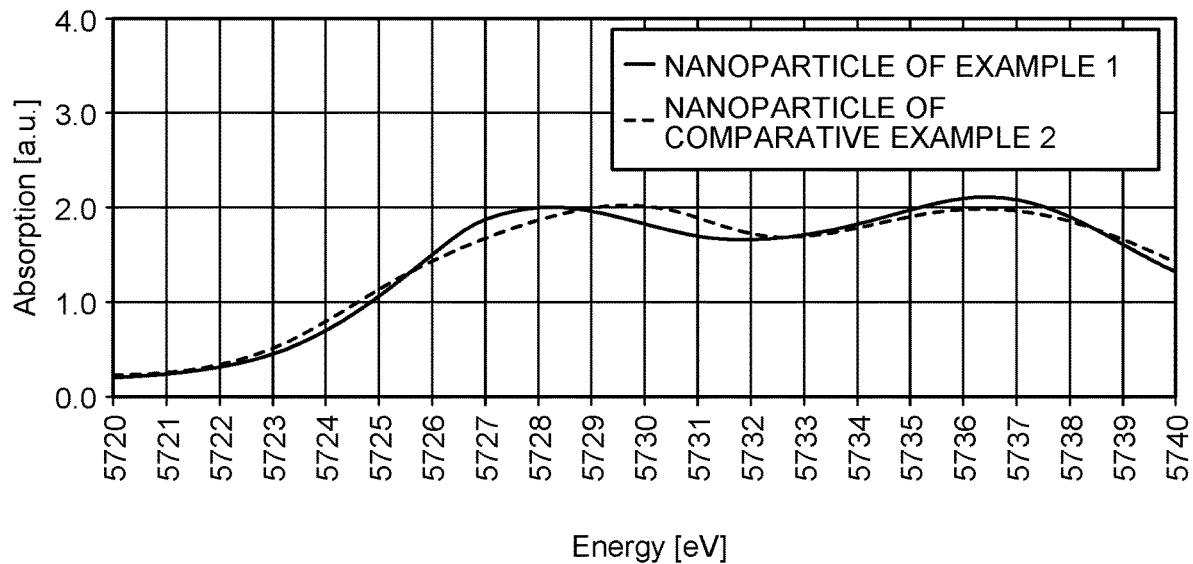
FIG. 1 is the CeL3 edge XANES spectra of the cerium oxide nanoparticles prepared in Example 1 and Comparative Example 2, as measured in Example 18.

The dispersion body containing the cerium oxide nanoparticle is sometimes described as the dispersion body or the dispersion solution.

In the synthesis of the cerium oxide nanoparticle, one of the raw materials is a water-soluble salt of cerium. So, the synthesis is carried out in water or a solvent compatible with water. From a viewpoint of compatibly having an appropriate hydrophilicity and a property that allows formation of an amine complex with a metal ion, a preferred example of the aromatic heterocyclic compound is the one that contains 2 to 8 carbon atoms and 1 to 4 nitrogen atoms in the ring structure thereof. At least one of the above-mentioned nitrogen atoms is preferably the nitrogen atom having a lone electron pair that is not included in the π-conjugated system. A more preferred example of the aromatic heterocyclic compound to be used is that, in addition to the above features, it is a monocyclic or a bicyclic compound having a five-membered and/or a six-membered ring structure. In one example, illustrative examples of the aromatic heterocyclic compound described above include pyrazole, imidazole, triazole, pyridine, pyridazine, pyrimidine, pyrazine, triazine, tetrazine, indazole, benzimidazole, azaindole, pyrazolopyrimidine, purine, benzotriazole, quinoxaline, cinnoline, quinazoline, phthalazine, naphthyridine, and pteridine. The above aromatic heterocyclic compounds may be derivatives having the substituent such as a methyl group, an ethyl group, an amino group, an aminomethyl group, a monomethylamino group, a dimethylamino group, and a cyano group. These are substituents that do not significantly change the form of complexation or solubility in a reaction solvent.

The cerium oxide nanoparticle is composed of a mixture of $Ce_2O_3$ and $CeO_2$. It has been known that cerium oxide can actually include the forms of a hydroxide and an oxyhydroxide, in addition to the above oxide forms. The ratio of $Ce_2O_3$ to $CeO_2$ can be calculated as the ratio of cerium (III) to cerium (IV) by an X-ray photoelectron spectroscopy (XPS) or other methods.

The cerium oxide nanoparticle or the dispersion body containing the particle is produced by mixing a solution of an aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in the ring structure thereof, with a solution containing a cerium (III) ion or with a cerium (III) salt followed by addition of an oxidant. Hereinafter, the method of producing the cerium oxide nanoparticle or the dispersion body containing the particle will be explained.

The first process is to obtain a mixture solution by mixing a solution of an aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in the ring structure thereof (sometimes "aromatic heterocyclic compound") with a solution containing a cerium (III) ion or with a cerium (III) salt. The solution of the aromatic heterocyclic compound to be used in this process may be prepared by dissolving the aromatic heterocyclic compound into an arbitrary solvent. The solvent is preferably water or a water-compatible solvent. Specifically, illustrative examples of the water-compatible solvent include methanol, ethanol, propanol, isopropanol (2-propanol), butanol, tert-butanol, tetrahydrofuran, acetone, dimethylformamide (DMF), dimethyl sulfoxide (DMSO), glycerol, ethyleneglycol, and oligoethyleneglycol. When pyrazole, imidazole, triazole, pyridine, pyridazine, pyrimidine, pyrazine, triazine, or tetrazine is used, it is preferable that this compound be dissolved in water; and when indazole, benzimidazole, azaindole, pyrazolopyrimidine, purine, benzotriazole, quinoxaline, cinnoline, quinazoline, phthalazine, naphthyridine, or pteridine is used, it is preferable that this compound be dissolved in 50% ethyleneglycol. When the aromatic heterocyclic compound cannot be readily dissolved, this may be dissolved by heating or by an ultrasonic treatment.

The amount of the aromatic heterocyclic compound may be 0.1 to 100 molar equivalents relative to the cerium (III) ion.

Mixing of the solution of the aromatic heterocyclic compound with the solution containing a cerium (III) ion or with a cerium (III) salt may be effected by mixing the solution of the aromatic heterocyclic compound with the solution containing the cerium (III) ion after these solutions were prepared separately in advance. Or, alternatively, when the solvent of the aromatic heterocyclic compound is water or a water-compatible solvent, the cerium (III) salt may be added to the solution of the aromatic heterocyclic compound for mixing. The solution containing the cerium (III) ion may be prepared by dissolving the cerium (III) salt into an arbitrary solvent. As for the cerium (III) salt, for example, cerium (III) nitrate hexahydrate may be used.

The amount of the cerium (III) salt mixed with the solution of the aromatic heterocyclic compound may be such that the final concentration thereof in the reaction solution becomes 0.01% to 10% by mass. It is preferable that the resulting mixture solution be mixed for 5 minutes or longer until the solution becomes homogeneous.

In the first process, the solution containing the aromatic heterocyclic compound and the cerium (III) ion is preferably free from a trivalent or higher carboxylic acid such as the compounds listed below. Even when such a compound is contained, the amount thereof is preferably 0.1 equivalent or less, while more preferably 0.01 equivalent or less, relative to the cerium (III) ion. Trivalent or higher carboxylic acids are specifically nitrilotriacetic acid (NTA), ethylenediaminetetraacetic acid (EDTA), ethylenediaminedisuccinic acid (EDDS), glycol ether diamine tetraacetic acid (EGTA), diethylenetriamino pentaacetic acid (DTPA), citric acid, hydroxyethyl ethylenediaminetetraacetic acid (HEDTA), polyacrylic acid and/or their salts.

In the second process, an oxidant is added into the mixture solution obtained in the first process. Illustrative examples of the oxidant to be used in the second process include nitric acid, potassium nitrate, hypochlorous acid, chlorous acid, chloric acid, perchloric acid, halogens, hydrogen halides, permanganate salts, chromic acid, dichromic acid, oxalic acid, hydrogen sulfide, sulfur dioxide, sodium thiosulfate, sulfuric acid, and hydrogen peroxide. Among these, hydrogen peroxide is especially preferable. The addition amount thereof relative to the cerium (III) ion as the molar equivalent may be 0.1 to 10 equivalents, while preferably 0.5 to 2 equivalents.

When the oxidant is added to the mixture solution of the aromatic heterocyclic compound with the cerium (III) ion, the cerium (III) ion is oxidized to cerium (IV), thereby starting the reaction to form the cerium oxide particle consisting of a mixture of $Ce_2O_3$ and $CeO_2$. During this reaction, the solution is colored in yellow, orange, red, brown or the like. This coloring takes place because the cerium (III) ion changes to cerium (IV), in which the coloring degree is determined by the ratio of cerium (III) to cerium (IV) that are present on the surface of the cerium oxide nanoparticle. Termination of the reaction can be judged at the time when the color does not change any further. The particle formation reaction depends on pH. The reaction proceeds in a weakly acidic to a basic solution. The pH shifts to the acidic side as the reaction progresses. So, during the time from the addition of the oxidant until the end of the reaction, it is preferable to keep the reaction solution at pH 5 or higher, more preferably at pH 6 or higher, while still more preferably at pH 7 or higher. To adjust the pH, an aqueous sodium hydroxide solution or an aqueous ammonia solution may be used. The reaction is usually completed in about 5 minutes to about 1 hour. Then, the dispersion body containing the cerium oxide nanoparticle is obtained. For example, when 200 µl of an aqueous solution of 10% by mass cerium (III) nitrate hexahydrate is added to a solution of 9.5 mg/10 ml 1,2,4-triazole, followed by addition of 200 µl of an aqueous solution of 1.2% by mass hydrogen peroxide and stirring the resulting mixture at room temperature, the solution turns to an orange color, and the reaction is completed in about 10 minutes.

As for the dispersion body, the dispersion solution after completion of the reaction may be used as it is. Alternatively, this may be used after the unreacted oxidant, the cerium (III) ion, and the excess aromatic heterocyclic compound that remain in the dispersion solution after completion of the reaction are removed by filtrating using an ultrafiltration membrane or by dialyzing using a semi-permeable membrane. Thereafter, the dispersion body may be dried using an evaporator or a freeze dryer to extract the cerium oxide nanoparticle.

In addition to the cerium oxide nanoparticle and water as the solvent, the dispersion body may include other solvent components that are compatible with water. Illustrative examples thereof include methanol, ethanol, propanol, isopropanol (2-propanol), butanol, tert-butanol, tetrahydrofuran, acetone, dimethylformamide (DMF), dimethyl sulfoxide (DMSO), glycerol, ethyleneglycol, and oligoethyleneglycol. These solvent components may be included to be 90% or less by volume. These solvent components may be added to the dispersion solution after completion of the reaction, or added after filtration by an ultrafiltration membrane, or used as a dialysate, or added to the dispersion solution after dialysis. This may also be added to the dried cerium oxide nanoparticle to make a dispersion solution.

The dispersion body may include an ionic component. The ionic component may be, as the component that imparts a buffering property, acetic acid, phthalic acid, succinic acid, carbonic acid, tris(hydroxymethyl)aminomethane (Tris), 2-morpholinoethanesulfonic acid monohydrate (MES), bis (2-hydroxyethyl)iminotris(hydroxymethyl)methane (Bis-Tris), N-(2-acetamido)iminodiacetic acid (ADA), piperazine-1,4-bis(2-ethanesulfonic acid) (PIPES), N-(2-acetamido)-2-aminoethanesulfonic acid (ACES), 2-hydroxy-3-morpholinopropanesulfonic acid (MOPSO), N,N-bis(2-hydroxyethyl)-2-aminoethanesulfonic acid (BES), 3-morpholinopropanesulfonic acid (MOPS), N-tris(hydroxymethyl)methyl-2-aminoethanesulfonic acid (TES), 2-[4-(2-hydroxyethyl)-1-piperazinyl]ethanesulfonic acid (HEPES), 2-hydroxy-N-tris(hydroxymethyl)methyl-3-aminopropanesulfonic (TAPSO), piperazine-1,4-bis(2-hydroxy-3-propanesulfonic acid) (POPSO), 2-hydroxy-3-[4-(2-hydroxyethyl)-1-piperazinyl]propanesulfonic acid (HEPSO), 3-[4-(2-hydroxyethyl)-1-piperazinyl]propanesulfonic acid (HEPPS), (Tricine), N,N-bis(2-hydroxyethyl)glycine (Bicine), or N-tris(hydroxymethyl)methyl-3-aminopropanesulfonic acid (TAPS). As for the component that does not impart a buffering property, sodium chloride and potassium chloride may be mentioned. These ionic components can be added such that the final concentrations thereof may be 0.1 mM to 1 M. These ionic components may be added to the dispersion solution after completion of the reaction, or added after filtration by an ultrafiltration membrane, or used as a dialysate, or added to the dispersed solution after dialysis. This may be added to the dried cerium oxide nanoparticle to make it a dispersion body.

The pH of the dispersion body may be adjusted after purification. The pH of the dispersion body may be 2 to 12, preferably 4 to 10, while more preferably 5 to 8. The pH may be adjusted by adding a buffer solution, an acid such as nitric acid, sulfuric acid, or hydrochloric acid, or a base such as sodium hydroxide or potassium hydroxide.

The dispersion body may be stored as the dispersion solution after completion of the reaction as it is, or this may be stored as a purified product having the dispersion solution after completion of the reaction filtrated by an ultrafiltration membrane, or as a purified product having been dialyzed by a semi-permeable membrane. Also, this may be stored as a dispersion solution containing the above solvent and ionic component, or this may be stored after pH thereof is adjusted. When this is stored as the dispersion solution, this is stored preferably under a refrigerated condition.

The cerium oxide nanoparticle can be obtained as a dry product by taking it out from the dispersion body produced followed by drying as described above. For example, the solution after completion of the reaction is filtrated by an ultrafiltration membrane or dialyzed by a semi-permeable membrane to remove the unreacted oxidant, the cerium (III) ion, and the excess aromatic heterocyclic compound that remain in the solution after completion of the reaction. Then, this is dried by using an evaporator, a freeze dryer or the like to obtain the cerium oxide nanoparticle. Specifically, ultrafiltration membranes such as Amicon Ultra from Merck and Vivaspin from GE Healthcare, and semi-permeable membranes such as Spectra/Pore from Spectrum Inc. may be used. The taken-out dispersion body may be dried under the temperature and atmospheric pressure conditions at which the solvent becomes a gas in the phase diagram. For example, when the nanoparticle is water dispersed, the evaporator may be set to 40° C. and 50 hPa or less to remove water. As for the evaporator, for example, N-1200A manufactured by Tokyo Rika Kikai Co., Ltd. may be used. Also, water may be removed by setting a freeze dryer at −40° C. and 20 Pa. As for the freeze dryer, for example, FDU-1200 manufactured by Tokyo Rika Kikai Co., Ltd. may be used. In addition, drying may be carried out by heating at 100° C. or higher in an oil bath, or at 80° C. or higher in a thermostatic dryer.

The hydrodynamic diameter of the cerium oxide nanoparticle in the dispersion body is calculated as the average particle diameter by measuring the dynamic light scattering thereof to obtain the autocorrelation function followed by analyzing this with the Marquadt method. So, the calculation is made from the number conversion histogram thereof. Measurement of the dynamic light scattering is done by using ELS-Z manufactured by Otsuka Electronics Co., Ltd. The hydrodynamic diameter of the cerium oxide nanoparticle in the dispersion solution may be 1 to 1000 nm, while preferably 1 to 200 nm.

The hydrodynamic diameter of the cerium oxide nanoparticle in the dispersion body may be adjusted by the molar equivalent of the aromatic heterocyclic compound relative to the cerium (III) ion. The lower the molar equivalent is, the larger the diameter of the particle is obtained. And, the higher the molar equivalent is, the smaller the diameter of the particle is obtained.

The energy states of cerium (III) and cerium (IV) in $Ce_2O_3$ and $CeO_2$ may be observed by measurement of the X-ray absorption fine structure (XAFS) spectrum. In the XAFS spectrum, the structure at about 20 eV from the absorption edge is called XANES (X-ray absorption near edge structure), and the extended X-ray absorption fine structure appearing at more than about 100 eV on a high-energy side from the absorption edge is called EXAFS (extended X-ray absorption fine structure). From XANES, the information relating to the valency and structure of the focused atom can be obtained; from the EXAFS analysis, the information relating to the local structure of the sample, as well as the atom species, valency, and distance around the focused atom can be obtained by Fourier transformation of the actual spectrum (corresponding to FT-EXAFS/dynamic radial distribution function). The energy states of cerium (III) and cerium (IV) in the oxidation reduction reaction of cerium oxide are reflected in the peak positions and peak intensity ratio of the maximum absorptions in the XANES spectrum.

The cerium oxide nanoparticle has the maximum absorptions of 5726.0 to 5729.0 eV and 5735.0 to 5739.0 eV in the CeL3 edge XANES spectrum obtained by measurement of the X-ray absorption fine structure spectrum.

The dispersion body may be sterilized prior to use. Sterilization may be conducted by the method in which the dispersion solution is passed through a sterilizing filter.

The cerium oxide nanoparticle or the dispersion body containing the nanoparticle may be used as an oxidant. For example, by utilizing the oxidative action thereof, this may be used as a homogeneous catalyst in an organic synthetic reaction and in a polymer polymerization, as well as in a solution for wet-etching of a semiconductor. By utilizing the oxidative action thereof, this may be used as the solution that substitutes an oxidative enzyme solution. Specifically, this may be used as a substitute of an oxidase or a peroxidase in a detection reaction or in a tissue dyeing using an antibody-antigen reaction or a nucleic acid hybridization, or in an electrochemical detection reaction by coating this thereby immobilizing the cerium oxide nanoparticle onto an electrode. In addition to these, by utilizing the oxidative action thereof, this may be used for decomposition and removal of a dirt, a smell, an allergen, a virus, a bacterium, a fungus, and a mold, as a bleaching agent or as a disinfectant. Specifically, as the bleaching agent, this may be used for cleaning of clothes, tableware, a kitchen, a toilet, a washroom, a bathroom, medical equipment, and so forth. Also, this may be added as the disinfectant to a swimming pool, a bathtub, and a hot spring. Furthermore, this may be used as a body soap, a hand cleaning material, a disinfecting medicine, a gargle, a mouth washer, and so forth. The performance of this as the oxidant described above may be evaluated by the color fading reaction of an organic dye or the like, which will be described later.

In other examples, the cerium oxide nanoparticle or the dispersion body containing this nanoparticle may be added to a fiber, a tube, a bead, a rubber, a film, a plastic and the like during molding as the additive to impart an oxidative performance, or may be applied to their surfaces for odor control, anti-allergic, antiviral, antibacterial, and anti-fungal processing. Illustrative examples of the processed product using the nanoparticle or the dispersion body include a radially-cracked cover of the drain hole in a kitchen sink, a drain plug, a sealing material for window glazing, a sealing material for attaching a mirror, a water-proof sealing material in a bathroom, in a washing stand, and in a kitchen, an inner sealing material of a refrigerator door, a bath mat, an anti-sliding rubber of a washing bowl and a chair, a hose, a shower head, a sealing material used in a water purifier, a plastic product of a water purifier, a packing material used in a clothes washing machine, a plastic product used in a clothes washing machine, a mask, a cap for medical use, a shoes cover for medical use, an air conditioner filter, a filter of air cleaning equipment, a filter for a vacuum cleaner, a filter for a ventilation fan, a filter for a vehicle, a filter for an air conditioner, a fin of an air conditioner, plastic parts such as a louver of an air conditioner's blowing outlet and a blowing fan, a fin of a car air conditioner, plastic parts such as a louver of a car air conditioner's blowing outlet and a blowing fan, clothes, bedding clothes, a net in a screen door, a net for a chicken house, a net such as a mosquito net, a wall paper and a window, a blind, an interior material of a building such as a hospital, an interior material of a train and a car, a seat for a vehicle, a blind, a chair, a sofa, virus-treating equipment, and a construction material for a door, a ceiling, a floor, a window and the like. Thus, products that are processed using the nanoparticle or the dispersion body can be used in various fields as hygienic materials.

The color fading reaction of the organic dye can also be used for evaluation of the photocatalytic performance of titanium oxide. The decomposition rate of the dye thereby obtained can be used as the indicator of the characteristic with regard to the oxidative decomposition of an organic substance. Specifically, the decomposition rate of the dye is calculated as follows. First, the dispersion body is mixed with an organic dye such as Acid Orange 7 (AO7). Then, the resulting mixture solution is allowed to statically leave for a prescribed period. As a control, the AO7 solution not including the cerium oxide nanoparticle is treated similarly. After the reaction, the absorption spectra of all the solutions are measured. For analysis, the absorbance at 485 nm, which is the maximum absorption wavelength of AO7, is used. The ratio of the difference value between the absorbance of the control and the absorbance of the solution containing the dispersion body to the absorbance of the control is calculated as the decomposition rate.

Also, a suitable example of the oxidant is the dispersion solution containing the aromatic heterocyclic compound and the cerium oxide nanoparticle having a decomposition rate of 30% or greater in the decomposition reaction of Acid Orange at 40° C. for 1 hour, the aromatic heterocyclic compound having no substituent or at least one substituent selected from the group consisting of a methyl group, an ethyl group, an amino group, an aminomethyl group, a monomethylamino group, a dimethylamino group, and a cyano group, and having 2 to 8 carbon atoms and 1 to 4 nitrogen atoms in the ring structure. When the decomposition rate in the decomposition reaction of Acid Orange at 40° C. for 1 hour is 30% or greater, this can be used as the oxidant. The decomposition rate in the decomposition reaction of Acid Orange at 40° C. for 1 hour is preferably 50% or greater, while especially preferably 70% or greater.

The cerium oxide nanoparticle or the dispersion body containing this nanoparticle may be used as the antioxidant. The antioxidant means the substance having a reductive property, thereby suppressing excessive oxidation of a lipid or reacting with a reactive oxygen (superoxide ion, hydroxy radical, hydrogen peroxide and the like) to suppress the action thereof (Standard Dictionary of Chemical Terms; second edition, Maruzen Publishing Co., Ltd.). For example, by utilizing the anti-oxidative action as described above, this may be used as a reducing agent in an organic reaction or as a radical terminating agent in polymer polymerization. By utilizing the anti-oxidative action, this may be used to protect cells from an oxidative stress by adding to a cell culture medium or applying to a culture vessel such as a Petri dish. In addition, this may be used to protect a skin from a lipid peroxide and a reactive oxygen when applied to the skin as a cosmetic. On top of these, by utilizing the anti-oxidative action, this may be used as the substitute of an anti-oxidative enzyme solution. Specifically, as a substitute of a catalase solution, this may be used in a detection reaction of hydrogen peroxide or in an electrochemical detection reaction by coating the dispersion solution to an electrode to immobilize the cerium oxide nanoparticle. In addition, this may be used as a neutralizing solution of hydrogen peroxide that is used in an industry such as foods, semiconductor, textile, pulp and paper manufacturing, as well as for sterilization of a public bath and removal of slime in a piping. These performances may be evaluated by the catalase activity and the like, which will be described later. In addition, the dispersion body may be added as the antioxidant at the time of molding a rubber and a plastic material; and this may also be added to a fuel, a detergent, foods, and an animal feed. The performance as the antioxidant as described above may be evaluated by a scavenging reaction or like of a reactive species, which will be described later.

Furthermore, the cerium oxide nanoparticle or the dispersion body containing this nanoparticle may be used in a drug to treat an oxidative stress or an inflammation of a human or of an animal as an antioxidant. Specifically, the dispersion body can be used for prevention and treatment of a disease that relates to the oxidative stress such as apoplectic stroke, disseminated sclerosis, amyotrophic lateral sclerosis, and ischemia reperfusion damage by administering the dispersion body to a test object by a topical, an enteral, or a parenteral method such as injection, drip infusion, or transplantation. Also, the dispersion body may reduce inflammation topically or systemically by coating this as the antioxidant on the surface of an artificial organ represented by a dialysis membrane and medicinal equipment such as a cannula, a catheter, and a stent.

The value of the catalase activity may be obtained in accordance with the protocol using AmplexRed Catalase Assay Kit (A22180), manufactured by Thermo Fisher Scientific Inc., as described in Japanese Translation of PCT International Application No. 2018-508568. The Reaction Buffer included in the kit, the dispersion body, and the aqueous hydrogen peroxide solution are mixed. Then, the resulting mixture is allowed to statically leave for 30 minutes to carry out the decomposition reaction of hydrogen peroxide. The reaction solution is passed through a 30 kD ultrafiltration membrane. Then, the flow-through solution is mixed with Working Solution included in the kit to carry out the reaction at 37° C. for 30 minutes. The resorufin generated by the reaction is excited at 544 nm, and the fluorescence intensity at 590 nm is measured. By comparing with the calibration curve of the catalase standard that is included in the kit, the activity value thereof being known, the catalase activity of the dispersion body is calculated. For measurement of the catalase activity, other kits such as EnzyChrom Catalase Assay Kit manufactured by BioAssay Systems, LLC may also be used.

A suitable example of the antioxidant is the dispersion solution of the cerium oxide nanoparticle that includes the aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in the ring structure, and the cerium oxide nanoparticle having concentration of 4 μg/ml and a catalase activity of 0.5 U/ml or higher in the degradation reaction of an aqueous hydrogen peroxide solution, measured by using AmplexRed Catalase Assay Kit (A22180) from Thermo Fisher Scientific Inc. When the catalase activity in the decomposition reaction of the aqueous hydrogen peroxide solution by using the AmplexRed Catalase Assay Kit (A22180) is 0.5 U/ml or higher, this can be used as the antioxidant. The catalase activity is preferably 0.7 U/ml or higher, while especially preferably 0.8 U/ml or higher.

The scavenging reaction of a reactive species may be measured as a dye retention rate by the method such as the one described in Y. Xue, J. Phys. Chem. C, 2011, 115, 4433-4438. Specifically, a hydroxy radical is generated by a Fenton reaction by mixing an aqueous iron (II) chloride solution with an aqueous hydrogen peroxide solution. Then, to this solution is added the dispersion body to carry out the radical scavenging reaction. This mixture solution is mixed with an organic dye such as methylene blue. Then, the resulting mixture is allowed to statically leave for a prescribed period. As a control, the same treatment is carried out to the solution not including the dispersion body. Furthermore, the methylene blue solution having the same concentration as that of the reaction solution is prepared as the standard solution. Then, the absorption spectra of these solutions are measured. For the analysis, the absorbance at 664 nm, which is the wavelength of the maximum absorption of methylene blue, is used. The difference ($\Delta I_0$) between the absorbance of the reference solution ($I_0$) and the absorbance of the control ($I_c$), and the difference ($\Delta I$) between the absorbance of the solution containing the dispersion body (I) and the absorbance of the control ($I_c$) is calculated. The ratio of the latter ($\Delta I$) to the former ($\Delta I_0$) is calculated as the decomposition rate. This is taken as the dye retention rate. This value is indicative of the radical scavenging performance. The dye retention rate may be obtained by using methyl violet in place of methylene blue.

EXAMPLES

Our nanoparticles, dispersion bodies, oxidants, antioxidants and methods will be explained more specifically by the following Examples.

Materials and Methods

Pyrazole, imidazole, 1-methylimidazole, 1,2,3-triazole, 1,2,4-triazole, 2-aminomethylpyridine, 2-cyanopyridine, 4-dimethylaminopyridine, pyridazine, pyrimidine, benzimidazole, adenine, and Acid Orange 7 were purchased from Tokyo Chemical Industry Co., Ltd. Pyridine, cerium (III) nitrate hexahydrate, and an aqueous 30% by mass hydrogen peroxide solution were purchased from FUJIFILM Wako Pure Chemical Corp. The commercially available cerium oxide dispersion solution (796077) used in the Comparative Examples was purchased from Merck. The AmplexRed Catalase Assay Kit (A22180) was purchased from Thermo Fisher Scientific Inc.

Other reagents were purchased from FUJIFILM Wako Pure Chemicals Coop., Tokyo Chemical Industry Co., Ltd., and Sigma-Aldrich Co., LLC. They were used as they were without any further purification.

For measurement of the hydrodynamic diameter of the dispersion solution containing the cerium oxide nanoparticle, the zeta potential and particle measurement system ELS-Z of Otsuka Electronics Co., Ltd. was used.

The heat block ND-SO1 was purchased from Nissinrika.

For absorbance measurement, the plate reader SpectraMax iD3 from MOLECULAR DEVICE, LLC was used.

Comparative Example 1

Dispersion Solution Containing Cerium Oxide Nanoparticle and Polyacrylic Acid as Stabilizing Agent With reference to A. Asati, Angew. Chem. Int. Ed. 2009, 48, 2308-2312, the cerium oxide nanoparticle was prepared to compare the oxidation activity. To 10 ml of the aqueous solution of 1% by mass of polyacrylic acid, 200 μl of the aqueous solution of 10% by mass of cerium (III) nitrate hexahydrate was added. Then, they were stirred at room temperature for 5 minutes. Next, 200 μl of the aqueous solution of 1.2% by mass of hydrogen peroxide was added. Then, the reaction was carried out by warming at 40° C. for 1 hour. The reaction solution was purified by using a 30 kD ultrafiltration membrane to obtain a yellow dispersion solution containing cerium oxide nanoparticles.

Example 1

Preparation of Dispersion Solution of Cerium Oxide Nanoparticle Containing Pyridine as Stabilizing Agent To 10 ml of the aqueous solution of 12 mg/10-ml of pyridine, 200 μl of the aqueous solution of 10% by mass of cerium (III) nitrate hexahydrate was added. Then, they were adjusted to pH 7 and stirred at room temperature for 5 minutes. Next, 200 μl of the aqueous solution of 1.2% by mass of hydrogen peroxide was added. Then, they were allowed to react at room temperature for 1 hour. The reaction solution was purified by using a 30 kD ultrafiltration membrane to obtain an orange-colored dispersion solution containing cerium oxide nanoparticles.

Example 2

Preparation of Dispersion Solution of Cerium Oxide Nanoparticle Containing Pyrazole as Stabilizing Agent The reaction was carried out under the same conditions as those of Example 1 except that the aqueous solution of 10 mg/10-ml pyrazole was used as the stabilizing agent in Example 1 to obtain an orange-colored aqueous solution containing cerium oxide nanoparticles.

Example 3

Preparation of Dispersion Solution of Cerium Oxide Nanoparticle Containing Imidazole as Stabilizing Agent The reaction was carried out under the same conditions as those of Example 1, except that the aqueous solution of 10 mg/10-ml imidazole was added as the stabilizing agent in Example 1 to obtain an orange-colored aqueous solution containing cerium oxide nanoparticles.

Example 4

Dispersion Solution of Cerium Oxide Nanoparticle Containing 1-Methylimidazole as Stabilizing Agent The reaction was carried out under the same conditions as those of Example 1, except that the aqueous solution of 12 mg/10-ml 1-methylimidazole was used as the stabilizing agent n Example 1 to obtain an orange-colored aqueous solution containing cerium oxide nanoparticles.

Example 5

Dispersion Solution of Cerium Oxide Nanoparticle Containing 1,2,3-Triazole as Stabilizing Agent The reaction was carried out under the same conditions as those of Example 1, except that the aqueous solution of 10 mg/10-ml 1,2,3-triazole was used as the stabilizing agent in Example 1 to obtain an orange-colored aqueous solution containing cerium oxide nanoparticles.

Example 6

Dispersion Solution of Cerium Oxide Nanoparticle Containing 1,2,4-Triazole as Stabilizing Agent The reaction was carried out under the same conditions as those of Example 1, except that the aqueous solution of 10 mg/10-ml 1,2,4-triazole was used as the stabilizing agent in Example 1 to obtain an orange-colored aqueous solution containing cerium oxide nanoparticles.

Example 7

Dispersion Solution of Cerium Oxide Nanoparticle Containing 2-(Aminomethyl)pyridine as Stabilizing Agent The reaction was carried out under the same conditions as those of Example 1 except that the aqueous solution of 16 mg/10-ml 2-(aminomethyl)pyridine was used as the stabilizing agent in Example 1 to obtain an orange-colored aqueous solution containing cerium oxide nanoparticles.

Example 8

Dispersion Solution of Cerium Oxide Nanoparticle Containing 2-Cyanopyridine as Stabilizing Agent The reaction was carried out under the same conditions as those of Example 1 except that the aqueous solution of 16 mg/10-ml 2-cyanopyridine was used as the stabilizing agent in Example 1 to obtain an orange-colored aqueous solution containing cerium oxide nanoparticles.

Example 9

Dispersion Solution of Cerium Oxide Nanoparticle Containing 4-Dimethylaminopyridine as Stabilizing Agent The reaction was carried out under the same conditions as those of Example 1 except that the aqueous solution of 19 mg/10-ml 4-dimethylaminopyridine was used as the stabilizing agent in Example 1 to obtain an orange-colored aqueous solution containing cerium oxide nanoparticles.

Example 10

Dispersion Solution of Cerium Oxide Nanoparticle Containing Pyridazine as Stabilizing Agent The reaction was carried out under the same conditions as those of Example 1 except that the aqueous solution of 12 mg/10-ml pyridazine was used as the stabilizing agent in Example 1 to obtain an orange-colored aqueous solution containing cerium oxide nanoparticles.

Example 11

Dispersion Solution of Cerium Oxide Nanoparticle Containing Pyrimidine as Stabilizing Agent The reaction was carried out under the same conditions as those of Example 1 except that the aqueous solution of 12 mg/10-ml pyrimidine was used as the stabilizing agent in Example 1 to obtain an orange-colored aqueous solution containing cerium oxide nanoparticles.

Example 12

Dispersion Solution of Cerium Oxide Nanoparticle Containing Benzimidazole as Stabilizing Agent The reaction was carried out under the same conditions as those of Example 1 except that a 50% aqueous ethyleneglycol solution of 18 mg/10-ml benzimidazole was used as the stabilizing agent in Example 1 to obtain an orange-colored aqueous solution containing cerium oxide nanoparticles.

Example 13

Dispersion Solution of Cerium Oxide Nanoparticle Containing Adenine as Stabilizing Agent The reaction was carried out under the same conditions as those of Example 1 except that the aqueous solution of 26 mg/10-ml adenine was used as the stabilizing agent in Example 1 to obtain an orange-colored aqueous solution containing cerium oxide nanoparticles.

Example 14

Measurement of Hydrodynamic Diameter of Dispersion Solution Containing Cerium Oxide Nanoparticle The hydrodynamic diameter of the dispersion solution containing the cerium oxide nanoparticle prepared in each of Examples 1 to 13 was measured by the dynamic light scattering (DLS) method. Water was used as the solvent for measurement. The average particle diameter of the hydrodynamic diameter was obtained in terms of number conversion. The obtained values are listed in Table 1.

TABLE 1

| Dispersion solution | Stabilizing agent | Solution | Hydrodynamic Diameter [nm] |
|---|---|---|---|
| Example 1 | Pyridine | Orange | 17.5 ± 6.4 |
| Example 2 | Pyrazole | Yellow | 28.7 ± 13.2 |
| Example 3 | Imidazole | Orange | 138.2 ± 27.3 |
| Example 4 | 1-Methylimidazole | Orange | 103.6 ± 24.6 |
| Example 5 | 1,2,3-Triazole | Orange | 121.2 ± 25.8 |
| Example 6 | 1,2,4-Triazole | Orange | 24.8 ± 8.2 |
| Example 7 | 2-(Aminomethyl)pyridine | Orange | 217.9 ± 90.2 |
| Example 8 | 2-Cyanopyridine | Pale yellow | 106.2 ± 28.0 |
| Example 9 | 4-Dimethylaminopyridine | Yellow | 180.3 ± 101.2 |
| Example 10 | Pyridazine | Yellow | 134.9 ± 34.6 |
| Example 11 | Pyrimidine | Yellow | 18.4 ± 2.5 |
| Example 12 | Benzimidazole | Orange | 13.5 ± 3.8 |
| Example 13 | Adenine | Orange | 106.9 ± 27.1 |

Example 15

Measurement of Oxidative Performance by Dye Degradation Test

30 µl of the aqueous solution of each of the dispersion solutions prepared in Examples 1 to 13 with the concentration thereof having been adjusted to 2 mg/ml, 60 µl of 0.5 mg/ml Acid Orange 7 (AO7) as the sample including the organic substance, and 1.41 ml of distilled water were added. Then, the resulting mixture was allowed to statically leave at 40° C. for 1 hour using the heat block to carry out the decomposition reaction of the dye. As the control, the AO7 solution not including the cerium oxide nanoparticle was treated in the same way as above. After the reaction, 100 µl of the solution was taken and diluted with 1.9 ml of distilled water. Then, the absorption spectrum thereof was measured. With regard to the sample of the control, there was no change found in the absorption spectrum before and after the heating.

In the analysis, the absorbance at 485 nm, which is the wavelength at the maximum absorption of AO7, was used. The difference value in the absorbance between the dispersion solution and the control was calculated. Then, the ratio of this difference value to the absorbance of the control was calculated as the decomposition rate. The results are listed in Table 2.

From this result, we confirmed that the dispersion solutions containing the cerium oxide nanoparticles of Examples 1 to 13 have the oxidative performance capable of decomposing the dye with a high decomposition rate.

On the other hand, the oxidative performances of the dispersion solution of the commercially available cerium oxide nanoparticle and of the dispersion solution of the cerium oxide nanoparticle prepared in Comparative Example 1 were measured in the same way, but degradation of the dye could be hardly observed.

TABLE 2

| Dispersion solution | Dye decomposition yield [%] |
|---|---|
| Example 1 | 71 |
| Example 2 | 45 |
| Example 3 | 88 |
| Example 4 | 56 |
| Example 5 | 51 |
| Example 6 | 75 |
| Example 7 | 58 |
| Example 8 | 46 |
| Example 9 | 46 |
| Example 10 | 36 |
| Example 11 | 34 |
| Example 12 | 95 |
| Example 13 | 53 |
| Commercially available product | 10 |
| Comparative Example 1 | 6 |

Comparative Example 2

Preparation of Dispersion Solution Containing Cerium Oxide Nanoparticle with Post Addition of Pyridine To compare the antioxidative performance of the dispersion solution containing the cerium oxide nanoparticle prepared by the method of Example 1 in which an oxidant was added in the copresence of the cerium (III) salt and pyridine as the stabilizing agent with that of the dispersion solution containing the cerium oxide nanoparticle prepared by the method different from Example 1, with reference to Japanese Translation of PCT International Application No. 2017-525658, the dispersion solution containing the cerium oxide nanoparticle was prepared by a production method in which pyridine was post-added to the cerium oxide nanoparticle to be adsorbed thereto.

A commercially available dispersion solution of the cerium oxide nanoparticle (IV) (Merck, 796077) was diluted to 0.2 mg/ml. Then, 12.2 mg of pyridine was added to 10 ml of this diluted solution, and they were stirred at room temperature for 1 hour. The resulting solution was then purified by using a 30 kD ultrafiltration membrane to obtain a brown aqueous solution containing cerium oxide nanoparticles.

Comparative Example 3

Preparation of Dispersion Solution of Cerium Oxide Nanoparticle Containing Citric Acid and EDDS as Stabilizing Agents To compare the antioxidative performance with that of the dispersion solution containing the cerium oxide nanoparticle prepared using the stabilizing agent that is different from that of our dispersion solution, with reference to Japanese Translation of PCT International Application No. 2018-508568, the dispersion solution containing the cerium oxide nanoparticle was prepared by using citric acid/EDDS as the stabilizing agents.

The pH of the aqueous solution obtained by dissolving 0.8 g of cerium nitrate, 0.24 g of citric acid monohydrate, and 0.41 g of EDDS into water was adjusted to 9.5 with the aqueous 30% ammonia solution. To this, 640 µl of the aqueous solution of 30% hydrogen peroxide was added dropwise. Then, the resulting mixture was stirred for 1 hour to obtain a brown aqueous solution. The solution was then purified by using a 3 kD ultrafiltration membrane to obtain a brown dispersion solution containing cerium oxide nanoparticles.

Comparative Example 4

Preparation of Dispersion Solution Containing Cerium Oxide Nanoparticle with Post Addition of Benzimidazole To compare the antioxidative performance of the dispersion solution containing the cerium oxide nanoparticle prepared by the method of Example 12 with that of the dispersion solution prepared by the method different from Example 12, the dispersion solution containing the cerium oxide nanoparticle was prepared by the manufacturing method in which benzimidazole was adsorbed by post-addition thereof to the cerium oxide nanoparticle (IV).

A brown aqueous solution containing cerium oxide nanoparticle was obtained with the same operation and conditions as those of Comparative Example 2, except that 18 mg of benzimidazole was used in place of pyridine and that the solvent of the aqueous solution of 50% ethylene glycol was used.

Example 16

Measurement of Antioxidative Performance by Catalase Activity Measurement

The catalase activity was measured by using AmplexRed Catalase Assay Kit (A22180) manufactured by Thermo Fisher Scientific Inc. in accordance with the protocol thereof. To describe simply, 50 µl of Reaction Buffer, 25 µl of the dispersion solution with the concentration of 16 µg/ml prepared in Examples 1 to 13, and 25 µl of the aqueous solution of 40 µM hydrogen peroxide were mixed. Then, the resulting mixture was allowed to statically leave for 30 minutes to carry out the decomposition reaction of hydrogen peroxide. The reaction solution was passed through a 30 kD ultrafiltration membrane. Then, 100 µl of the flow-through solution was mixed with 50 µl of Working Solution to carry out the reaction at 37° C. for 30 minutes. The resorufin generated by the reaction was excited at 544 nm, and the fluorescence intensity at 590 nm was measured. By comparing with the calibration curve prepared by the catalase standard whose activity value had already been known, the catalase activity of the dispersion solution was calculated. The results are listed in Table 3.

From this result, we confirmed that the dispersion solutions of the cerium oxide nanoparticles prepared in Examples 1 to 13 had high catalase activities.

On the other hand, the antioxidative performances of the dispersion solution prepared by post-adding pyridine in Comparative Example 2, the dispersion solution prepared by using a stabilizing agent that is different from that of our dispersion solution in Comparative Example 3, and the dispersion solution prepared by post-adding benzimidazole in Comparative Example 4 were measured in the same way. But the catalase activities of them were lower than those of our dispersion solutions.

TABLE 3

| Dispersion solution | Catalase activity [U/ml] |
| --- | --- |
| Example 1 | 0.7 |
| Example 2 | 0.5 |
| Example 3 | 0.8 |
| Example 4 | 0.6 |
| Example 5 | 0.5 |
| Example 6 | 0.8 |
| Example 7 | 0.6 |
| Example 8 | 0.5 |
| Example 9 | 0.5 |
| Example 10 | 0.5 |
| Example 11 | 0.5 |
| Example 12 | 1.3 |
| Example 13 | 0.5 |
| Comparative Example 2 | 0.3 |
| Comparative Example 3 | 0.2 |
| Comparative Example 4 | 0.2 |
| Reference Example 1 | 0.033 |

Reference Example 1

Estimation of Catalase Activity

Figure 2:
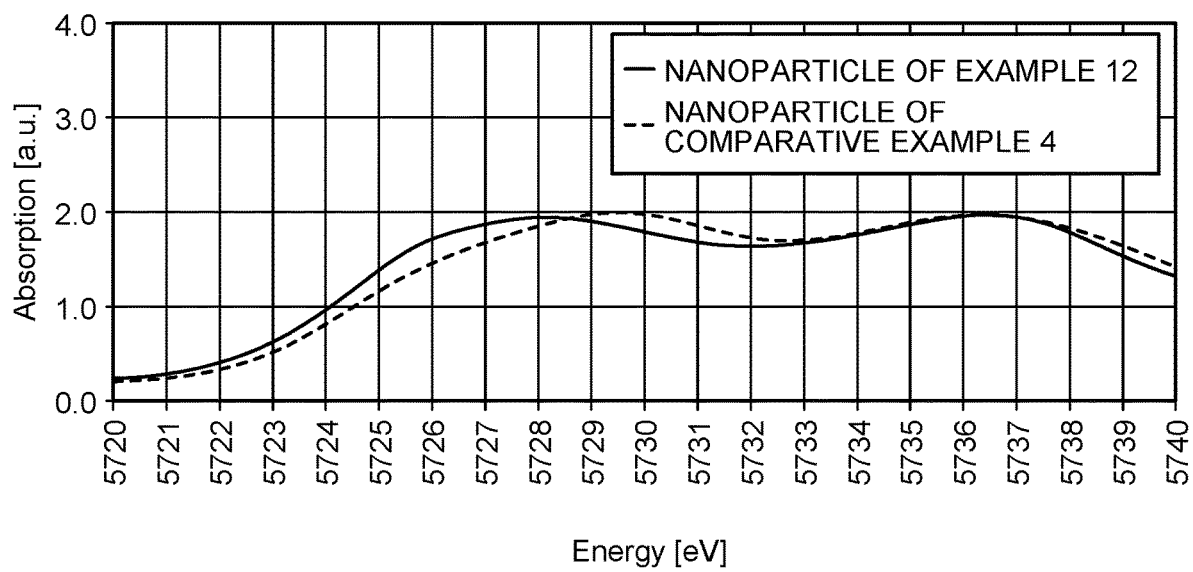
FIG. 2 is the CeL3 edge XANES spectra of the cerium oxide nanoparticles prepared in Example 12 and Comparative Example 4, as measured in Example 18.
Figure 3:
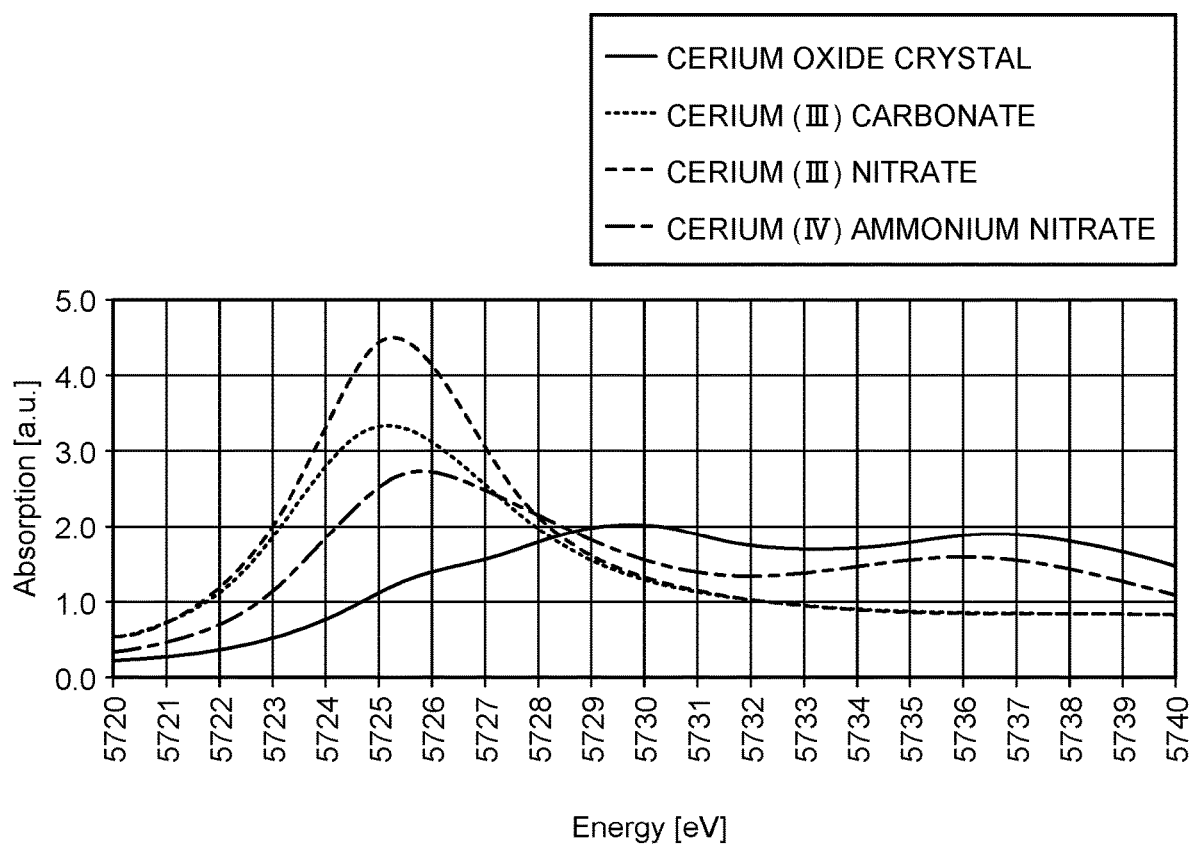
FIG. 3 is the CeL3 edge XANES spectra of the cerium oxide crystal, cerium (III) carbonate, cerium (III) nitrate, and cerium (IV) ammonium nitrate, as measured in Reference Example 2.

The catalase activity of the ceria nanoparticle composite described in Japanese Translation of PCT International Application No. 2015-518480 was estimated from FIGS. 2 and 3(a). Assuming from FIG. 2 that the volume of the solution is about 2 ml, and from FIG. 3(a) that the maximum of 1 M hydrogen peroxide is completely decomposed in 3 weeks. Therefore, 2 mmol of hydrogen peroxide is decomposed in 3 weeks so that the reaction rate is calculated to be about 0.066 µmol/min. Because 1 U of the catalase activity is 1 µmol/min, the activity thereof is about 0.066 U. Because the reaction volume is about 2 ml, the catalase activity of the ceria nanoparticle composite described in Japanese Translation of PCT International Application No. 2015-518480 is estimated to be about 0.033 U/ml. This estimated value is described in Table 3. Compared to our dispersion solutions prepared in Examples 1 to 13, the catalase activity of the ceria nanoparticle composite in Reference Example 1 was significantly lower.

Example 17

Measurement of Antioxidative Performance by Radical Scavenging Test Using 2,2-Diphenyl-1-picrylhydrazyl (DPPH)

The mixture was prepared by mixing 100 µl of the ethanol solution of 0.3 mM DPPH with 100 µl of our dispersion solution having a concentration of 0.5 mg/ml prepared in Example 12. Then, the resulting mixture was allowed to leave at room temperature for 30 minutes. As a control, the same treatment was carried out to the solution not containing the cerium oxide nanoparticle. The standard solution was prepared by mixing 100 µl of the ethanol solution of 0.3 mM DPPH with 100 µl of distilled water. Then, the absorption spectra of these solutions were measured.

For the analysis, the absorbance at 517 nm, which is the wavelength at the maximum absorption of DPPH, was used. The difference between the absorbance of the standard solution and the absorbance of the control, and the difference between the absorbance of our dispersion solution and the absorbance of the control were calculated. The ratio of the latter absorbance difference to the former absorbance difference was calculated as the DPPH retention rate (%). Then, the DPPH retention rate was subtracted from 100 to obtain the DPPH scavenging rate (%). The results are listed in Table 4.

From this result, we confirmed that our dispersion solution containing the cerium oxide nanoparticle has a high radical scavenging performance.

On the other hand, the dispersion solutions of the nanoparticles prepared in Comparative Examples 2 and 3 were measured for the radical scavenging performance in the same way. We found that the DPPH scavenging rates of them were lower than that of our dispersion solution.

TABLE 4

| Dispersion solution | DPPH scavenging rate (%) |
| --- | --- |
| Example 12 | 90 |
| Comparative Example 2 | 37 |
| Comparative Example 3 | 35 |

Example 18

XAFS Observation

An X-ray was irradiated to each of the dispersion solutions (8 mg/ml) of our cerium oxide nanoparticles prepared in Example 1 and 12. By measuring the absorption amount thereof, the X-ray absorption fine structure (XAFS) spectrum was measured. The measurement was carried out at the High Energy Accelerator Research Organization Synchrotron Radiation Research Center (Photon Factory) BL12C by the transmission detection method with the CeL3 absorption edge using the Si(111) double crystal spectrometer and the ion chamber detector.

The CeL3 edge XANES spectra thereof are exhibited in FIGS. 1 and 2. In the spectra, the absorption edge (E0) of the spectrum was set at 5724.4 eV, in which the vertical axis is the ratio based on 0 as the average absorption of −150 eV to −30 eV from E0, and 1 as the average absorption of +150 eV to +400 eV from E0.

The cerium oxide nanoparticle prepared in Example 1 had the maximum absorption at 5728.306 eV and 5736.407 eV, and the cerium oxide nanoparticle prepared in Example 12 had the maximum absorption at 5728.145 eV and 5736.246 eV. From this result, it became clear that our cerium oxide nanoparticle has the maximum absorptions of 5726.0 eV to 5729.0 eV and 5735.0 eV to 5739.0 eV.

Also, with regard to the solutions of the cerium oxide nanoparticle prepared in Comparative Examples 2 and 4, in which the preparation was carried out by post-addition of the stabilizing agent, the XAFS observation was carried out with the same operation and under the same conditions as those described above. The CeL3 edge XANES spectra thus obtained are exhibited in FIGS. 1 and 2.

The cerium oxide nanoparticle of Comparative Example 2 had the maximum absorption at 5729.426 eV and 5736.246 eV, and the cerium oxide nanoparticle of Comparative Example 4 had the maximum absorption at 5729.426 eV and 5736.407 eV. These cerium oxide nanoparticles were found to have the maximum absorption between 5735.0 eV and 5739.0 eV, but the maximum absorption was not found between 5726.0 eV and 5729.0 eV so that we found that these particles have the spectrum different from that of our cerium oxide nanoparticles.

Reference Example 2

XAFS Observation

The XAFS observation was carried out with the same operation under the same conditions as those of XAFS observation in Example 18, except that cerium oxide crystal, cerium (III) carbonate, cerium (III) nitrate, and cerium (IV) ammonium nitrate, which are not nanoparticles, were used. The CeL3 edge XANES spectra of them are exhibited in FIG. 3.

Cerium oxide crystal has the maximum absorptions at 5729.751 eV and 5736.582 eV, cerium (III) carbonate at 5725.161 eV, cerium (III) nitrate at 5725.316 eV, and cerium (IV) ammonium nitrate at 5725.796 eV and 5736.105 eV. In any of the cerium compounds, we found that there were no maximum absorptions between 5726.0 and 5729.0 eV and between 5735.0 and 5739.0 eV, contrary to our cerium oxide nanoparticles.

The invention claimed is:

1. A cerium oxide nanoparticle produced by 1) mixing a solution of an aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in a ring structure of the aromatic heterocyclic compound, with a solution containing a cerium (III) ion or with a cerium (III) salt, 2) followed by addition of an oxidant.

2. The cerium oxide nanoparticle according to claim 1, wherein a pH is adjusted to 5 or higher at the time when the oxidant is added.

3. The cerium oxide nanoparticle according to claim 1, wherein the aromatic heterocyclic compound is a monocyclic or a bicyclic compound having a five-membered and/or a six-membered ring structure.

4. The cerium oxide nanoparticle according to claim 1, wherein the compound is pyrazole, imidazole, triazole, pyridine, pyridazine, pyrimidine, pyrazine, triazine, tetrazine, indazole, benzimidazole, azaindole, pyrazolopyrimidine, purine, benzotriazole, quinoxaline, cinnoline, quinazoline, phthalazine, naphthyridine, or pteridine.

5. A dispersion body comprising the cerium oxide nanoparticle according to claim 1.

6. An oxidant comprising the dispersion body according to claim 5.

7. An antioxidant comprising the dispersion body according to claim 5.

8. An oxidant comprising the cerium oxide nanoparticle according to claim 1.

9. An antioxidant comprising the cerium oxide nanoparticle according to claim 1.

10. A cerium oxide nanoparticle comprising:
an aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in a ring structure of the aromatic heterocyclic compound, wherein the cerium oxide nanoparticle has maximum absorptions of 5726.0 eV to 5729.0 eV and 5735.0 eV to 5739.0 eV in a CeL3 edge XANES spectrum obtained by an X-ray absorption fine structure spectroscopy.

11. A dispersion body comprising the cerium oxide nanoparticle according to claim 10.

12. An oxidant comprising the cerium oxide nanoparticle according to claim 10.

13. An antioxidant comprising the cerium oxide nanoparticle according to claim 10.

14. A method of producing a cerium oxide nanoparticle comprising:
mixing a solution of an aromatic heterocyclic compound having no substituent or at least one substituent selected from the group consisting of a methyl group, an ethyl group, an amino group, an aminomethyl group, a monomethylamino group, a dimethylamino group, and a cyano group and containing 2 to 8 carbon atoms and 1 to 4 nitrogen atoms in a ring structure of the aromatic heterocyclic compound, with a solution containing a cerium (III) ion or with a cerium (III) salt; and adding an oxidant.

* * * * *